United States Patent [19]

Suh et al.

[11] 4,443,764
[45] Apr. 17, 1984

[54] METHOD FOR NON-DESTRUCTIVE DETECTION AND CHARACTERIZATION OF FLAWS

[75] Inventors: Nam P. Suh, Sudbury; Ming K. Tse, Cambridge, both of Mass.

[73] Assignee: Massachusetts Institute of Technology, Cambridge, Mass.

[21] Appl. No.: 202,331

[22] Filed: Oct. 30, 1980

[51] Int. Cl.³ .................................................. G01N 27/60
[52] U.S. Cl. ........................................ 324/456; 324/452
[58] Field of Search ................ 324/452, 454, 455, 456

[56] References Cited

U.S. PATENT DOCUMENTS 3,866,114 2/1975 Johnston ............................. 324/452
4,233,562 11/1980 Blythe ................................. 324/452

OTHER PUBLICATIONS

R. E. Collins, "Measurement of Charge Distribution in Electrets", Review of Scientific Instruments, vol. 48, No. 1, Jan. 1977, pp. 83-91.

Primary Examiner—Michael J. Tokar
Attorney, Agent, or Firm—Arthur A. Smith, Jr.; Robert F. O'Connell

[57] ABSTRACT

A method for the nondestructive testing and evaluation of insulating materials is disclosed. The method comprises applying an electrostatic charge pattern to one surface of the material; providing an electrode on a second surface opposite said one surface, said electrode being at an electrical potential lower than said one surface so that the electrostatic charge can decay through said material; allowing the charge pattern to decay for a predetermined period of time; and determining the residual charge pattern on said one surface after said period. The method preferably further comprises heating the material above room temperature which can enhance the results.

15 Claims, 23 Drawing Figures

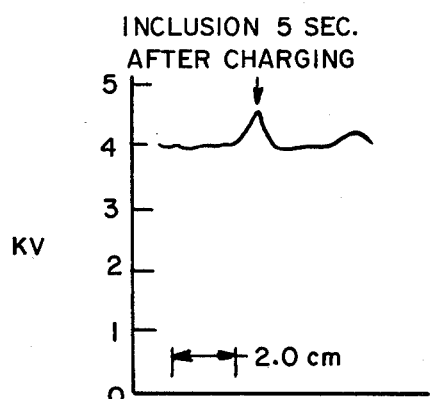
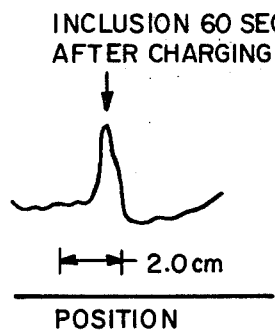
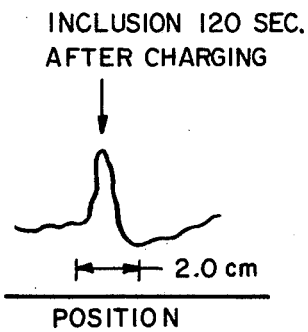
FIG.8A  FIG.8B  FIG.8C
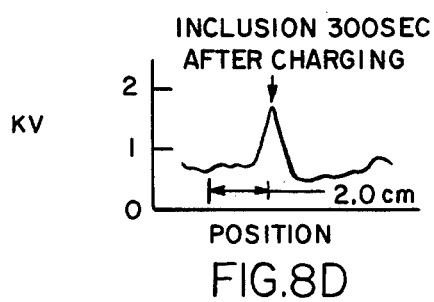
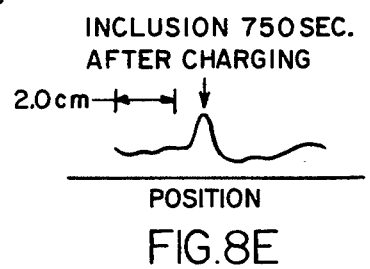
FIG.8D  FIG.8E
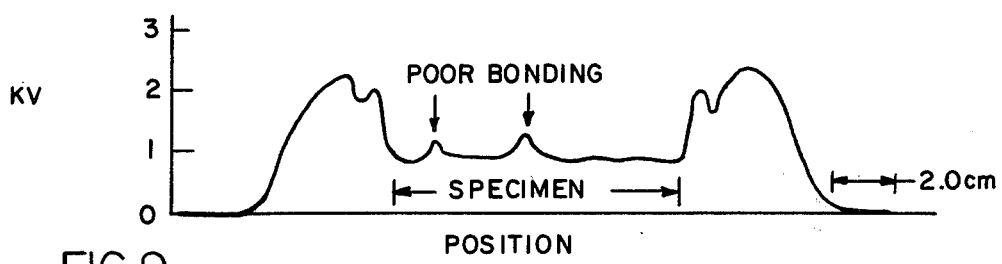
FIG.9
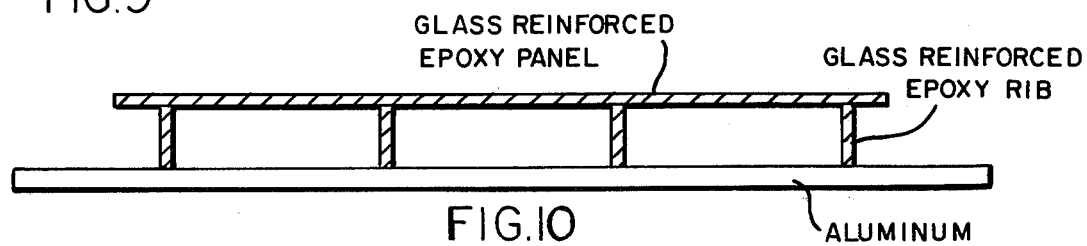
FIG.10
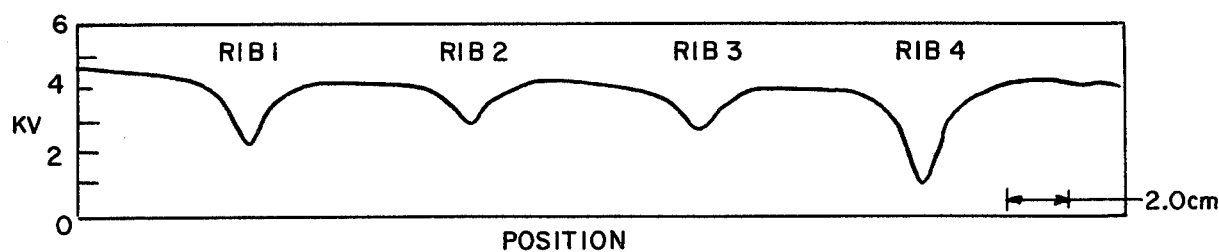
FIG.11

METHOD FOR NON-DESTRUCTIVE DETECTION AND CHARACTERIZATION OF FLAWS

FIELD OF THE INVENTION

This invention relates to methods for nondestructive evaluation of materials and particularly to a method for detecting and characterizing flaws in polymeric and other insulating materials.

BACKGROUND OF THE INVENTION

In many applications of polymeric materials, particularly in the use of polymeric composites in structural applications, it is necessary to have accurate knowledge of any existing flaw's size, shape and location. The use of polymeric composite materials has been increasing at a tremendous rate. The reasons for this trend are that these materials have very attractive strength-to-weight ratio and dimensional stability. To fully utilize the potential of these materials, nondestructive techniques for characterization of flaws are becoming key elements in the manufacturing processes and in-service maintenance of these materials. Moreover, to minimize inspection cost and to maximize inspection reliability and accuracy, an automated, on-line system is highly desirable.

Existing techniques such as ultrasonics, x-radiography, thermal imaging, microwave techniques, holographic techniques, and acoustic emisions are not suitable for on-line measurements. Notwithstanding advances in numerous NDE (nondestructive evaluation) techniques, notably in the use of ultrasonics, a fully automated, on-line inspection system is still not available for composite and polymeric materials. One of the major obstacles for developing an automated, on-line system is that interpretation of the measurement output in order to determine the nature and the characteristics of the defects is still a difficult problem. Moreover, most techniques can only be used at fairly low speed. For instance, ultrasonics, the work horse for inspection of composite materials, suffers from most of these problems, in addition to other questions on reproducibility of measurements and convenience in use. Other available techniques such as x-ray radiography, dye-penetrant, eddy current, thermal imaging techniques, corona and microwave methods, holographic techniques, and acoustic emissions, etc. suffer from one problem or another. For example, the ultrasonic technique requires a coupling medium between the ultrasonic transducer and the object-under-test for acoustic impedance matching; radiation hazard is a problem in using x-ray; microwave techniques can only be used for fairly large defects due to the long wavelength; and holographic technique using laser optics has stringent requirements on mechanical stability. Hence, there is a need for a technique which is sensitive and quantitative for detecting and characterizing defects. At the same time, this technique should be simple and low cost, thus lending itself to cost-effective, on-line inspection.

SUMMARY OF THE INVENTION

The present invention combines the advantages of being a non-destructive, high speed, non-contact and quantitive technique for location and estimation of the sizes of internal defects These advantages are important for an automated, on-line inspection system for polymeric parts.

Therefore, the present invention provides a method for the non-destructive detection of defects in an insulating material, said method comprising the steps of: applying an electrostatic charge pattern to one surface of the material; providing an electrode at a lower potential opposite said one surface so that charge can decay through said material; allowing the charge pattern to decay for a predetermined period of time; and determining the residual charge pattern on said one surface at the end of the time period.

The method is very sensitive because the electrical conductivities of materials can vary over many orders of magnitude, e.g. between the most conductive sustances (copper and silver) and the most resistive materials (polystyrene, for example) the difference amounts to 23 orders of magnitude. Further, a tiny amount of an impurity can change the conductivity many fold.

In an embodiment of the invention the material is heated above room temperature, either prior to applying the surface charge pattern or after applying said charge pattern but prior to determining the residual charge pattern, to increase the sensitivity of the method and to decrease the inspection time.

The thermal conductivity of materials, though not as dramatic as electrical conductivities, also varies over many orders of magnitude. The temperature dependence of the electrical conductivity of many polymeric materials follows an Arrhenius type thermally activated process. We have found that dramatic changes in the residual charge pattern can be produced by changes in temperature. In particular, we have found that, when a piece of material is heated from one side, the presence of a foreign material will perturb the temperature distribution and thus can enhance the sensitivity of this detection method.

Other means for accelerating charge decay can also be used, for example, incorporation of plasticizing agents, fillers, and antistatic agents.

BRIEF DESCRIPTION OF THE DRAWINGS

FIGS. 8A, 8B, 8C, 8D and 8E are graphs illustrating the change in surface charge as a function of time for a nylon 6/6 specimen having an epoxy inclusion.

FIG. 9 is a graph illustrating the surface charge of a specimen having an aluminum oxide-filled silicon rubber coating on an aluminum panel wherein areas of poor bonding are illustrated.

FIG. 10 is a composite structural element used to illustrate the method of the present invention for determining bond quality.

FIG. 11 is a graph illustrating the surface charge on the structure of FIG. 10.

DESCRIPTION OF THE INVENTION

In accord with the present invention an insulating material can be non-destructively evaluated for flaws. One surface of the material is electrostatically charged to a high potential. The charging can be accomplished using a wire-corona charger with the specimen moving relative to the charger or vice versa. Thus, a uniform surface charge can be provided on the specimen surface. Typically, the surface potential is raised to provide a field strength on the order of about $10^4$ to $10^5$ V/cm. across the specimen thickness. The initial surface potential will, however, vary with the material being tested. The potential must be sufficient to allow detection of the defects but not high enough to cause electrical breakdown of the material. An appropriate potential can readily be found by a few simple test runs.

The opposite surface of the material is conveniently maintained at electical ground. The electric field so established becomes the driving force for decay of the surface electrostatic charges. After a predetermined time lapse, the specimen surface is scanned by a non-contact electrostatic probe. The residual electrostatic charge pattern on the polymer surface maps the location and provides information on the nature and the characteristic dimensions of any existing flaw(s).

The time period that must elapse between charging and reading the residual charge pattern, is dependent upon the material being evaluated, the initial surface potential, the thickenss of the specimen, the temperature, etc. The time required to provide the required sensitivity can readily be determined by running a few tests under the conditions in which the evaluation will be made.

We have found that, for the temperature, voltage and thickness ranges of interest, the initial decay rate is directly proportional to the charge mobility and initial potential and inversely proportional to the square of the thickness of the specimen. Thus, if the charge mobility for a particular material is known, the proportionality constant can be quickly determined and the initial decay rate readily estimated for various conditions.

Heating the material under test can dramatically affect the results. Thus, testing at elevated temperatures (above room temperature) may be preferred, particularly for some materials with extremely low conductivity, or when time is important. When testing at elevated temperatures, a temperature in the range of from about 150° F. to about 230° F. is generally satisfactory for polymers. The best temperature for any particular test, however, will vary depending upon the material and other test conditions.

Figure 1:
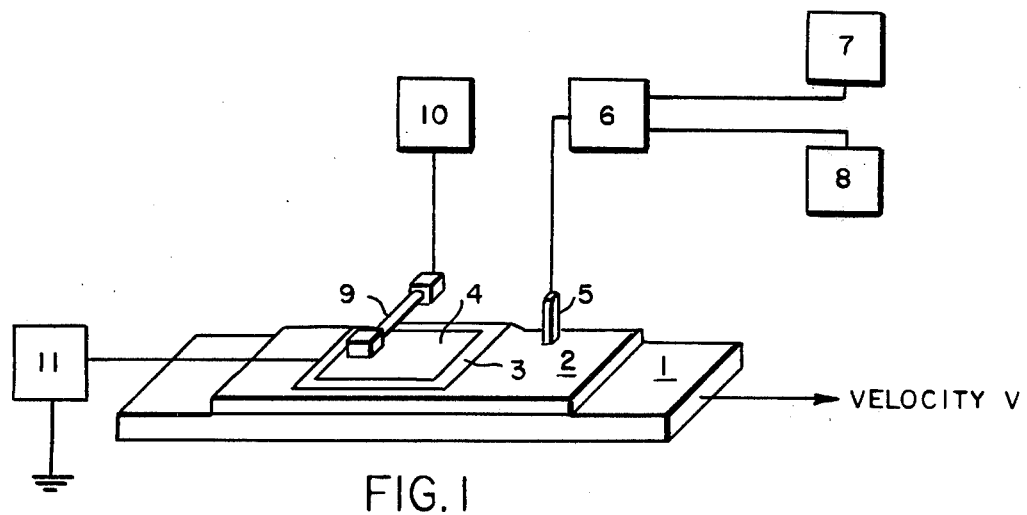
FIG. 1 is a schematic illustration of an apparatus for applying a charge pattern to a specimen and reading the residual charge pattern in accord with the present invention.

One apparatus useful for practicing this invention is illustrated in FIG. 1. The specimen 4 is positioned on an insulating platform 2 and is conveniently electrically grounded through a copper electrode layer 3. The insulating layer 2 is provided to insure that all current collected by the grounded electrode can be measured by electrometer 11. The platform is moved under a corona charger 9 that is coupled to a high voltage supply 10 to provide a uniform electrostatic charge pattern on the surface of the specimen. A suitable air gap is maintained between the charger and the specimen. One centimeter proved satisfactory for the gap in the examples that follow. The surface potential provided on the specimen depends upon a number of variables including the voltage supplied to the charger, the air gap, temperature, humidity, etc. The charged specimen can be heated by a resistive heater from the bottom or a radiant heater from the top.

Heating the specimen from the bottom surface has distinct advantages. The electrical conductivity, or more precisely, charge mobility, of polymers in general is strongly dependent on temperature. First, elevated temperature accelerates the decay of charges, thus speeding up the measurement process. Second, when the specimen is heated from the bottom surface, the perturbation of the one-dimensional heat flow by any internal defect (void or inclusion) leads to spatial variation in surface temperature. This effect, coupled with the temperature dependence of charge flaw rate, helps to differentiate between the regions containing flaws and normal regions in the specimen. In the apparatus of FIG. 1 the specimen 4 is conveniently heated from one side using a resistive foil heater under the electrical ground layer 3.

To determine the residual charge pattern the specimen is moved at constant velocity under an electrostatic probe and a profile of the electrostatic charge distribution on the specimen surface is obtained using electrostatic voltmeter 6, digital voltmeter 7, and strip-chart recorder 8. The presence of any defects (air voids or solid foreign inclusions, for example) are revealed as peaks or valleys in the charge profile.

This method for non-destructive evaluation of insulating materials is particularly suited for on-line use. Speeds up to 6.4 cm./sec. have been used for charging and scanning the specimen with no deterioration in charge uniformity or measurement sensitivity observed. Even higher speeds can be achieved with appropriate apparatus.

This invention will be illustrated further by the examples that follow. The examples were conducted using an apparatus as illustrated in FIG. 1 having a thin-wire (0.13 mm diameter, tungsten) corona charger, a variable voltage power supply (0–30 KV), a resistive foil heater, a temperature controller, a variable speed positioning system, an electrostatic voltmeter (Monroe Electronic, Model 168) and probe with digital readout, a chart recorder, and a Keithley electrometer (model 601C).

In using this apparatus, the charger and voltmeter probe are stationary. The specimen, positioned on the copper grounded electrode is moved continuously at a speed of 50 cm per minute at a charger-specimen separation of about 1 cm. A uniform electrostatic charge is thus built up on the polymer surface. The charged specimen is then brought up to the desire temperature by means of the resistive heating arrangement. At this time, the specimen is moved at a constant velocity under the electrostatic probe, thus obtaining a profile of the electrostatic charge distribution on the polymer surface.

Figure 2:
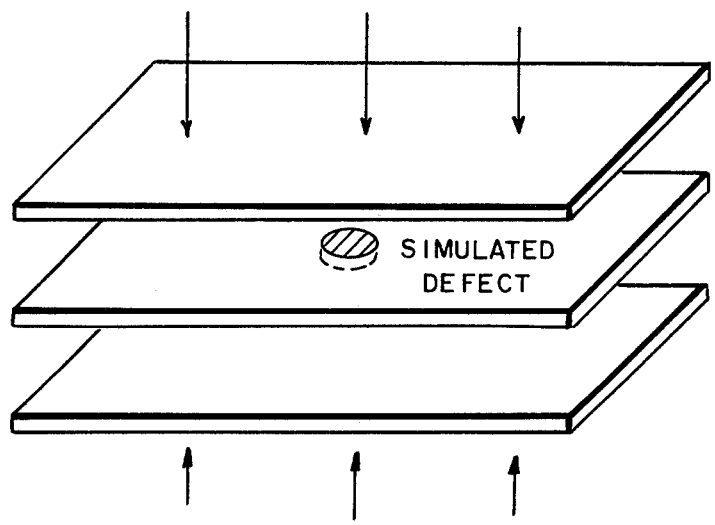
FIG. 2 is an exploded view of a specimen having a simulated flaw such as a void (gas) or an inclusion (solid).

Specimen are prepared as illustrated in FIG. 2. The total thickness of the specimen is about 1.6 mm and the thickness of the defect, which can be an inclusion or a void, is about 0.5 mm. Specimen having disc shaped defects with diameters ranging from about 1.6 mm to about 25.4 mm were made.

EXAMPLE 1

Figure 3A:
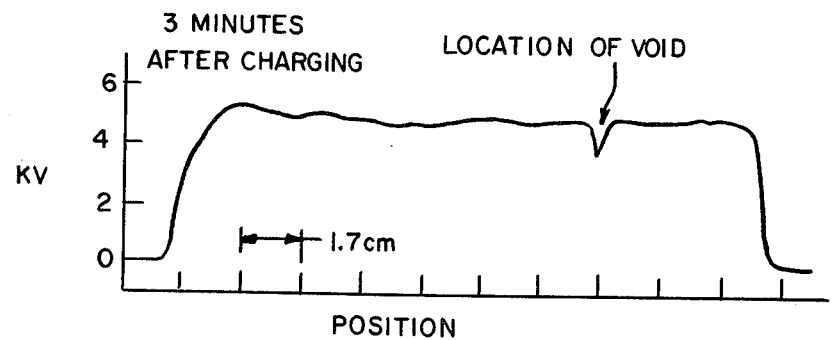
FIGS. 3A, 3B and 3C are graphs illustrating the residual surface potential across a polyethylene specimen having a 1.6 mm diameter disc-shaped void at various times after an initial charge is placed on the surface.
Figure 3B:
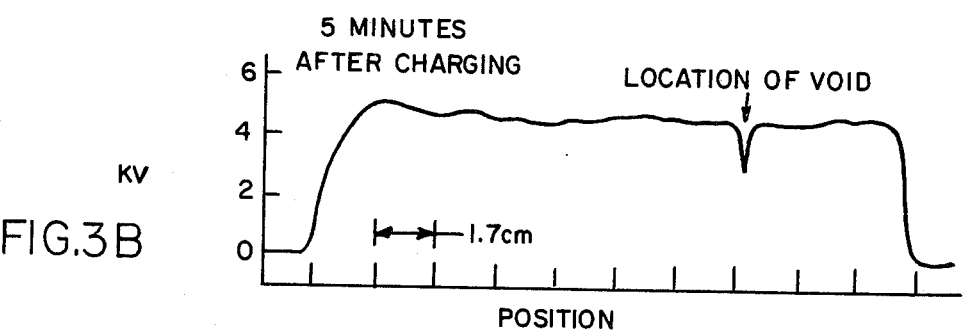
Figure 3C:
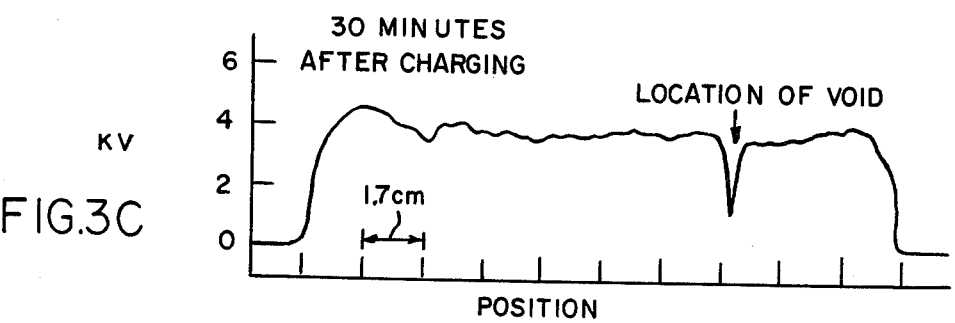

A specimen was prepared as shown in FIG. 2 using polyethylene sheets with a flaw made of a disc-shaped void having diameter of about 1.6 mm. The specimen was evaluated using the apparatus described above wherein the surface was charged using a corona voltage of 10 KV. The temperature of the specimen was then raised to 190° F. After a 3 minute time lapse, the surface potential profile shown in FIG. 3a was obtained. Note the depression in the profile at the area of the void defect. Surface potential profiles were again measured after time lapses of 5 and 30 minutes. See FIGS. 3b and 3c, respectively.

EXAMPLE 2

Figure 4:
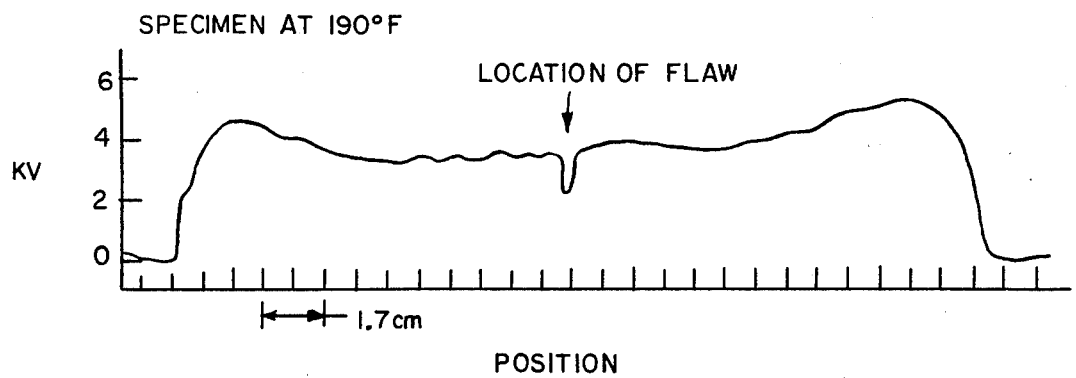
FIG. 4 is a graph illustrating the residual surface potential across a polyethylene specimen having a 1.6 mm diameter disc-shaped epoxy inclusion.

A specimen was prepared as in Example 1 except that the flaw was an epoxy inclusion of about 1.6 mm diameter. Upon charging at 10 KV as in Example 1 and a 30 minutes time lapse, the surface potential shown in FIG. 4 was obtained. Again the depression in the profile coincides with the inclusion defect.

EXAMPLE 3

Figure 5A:
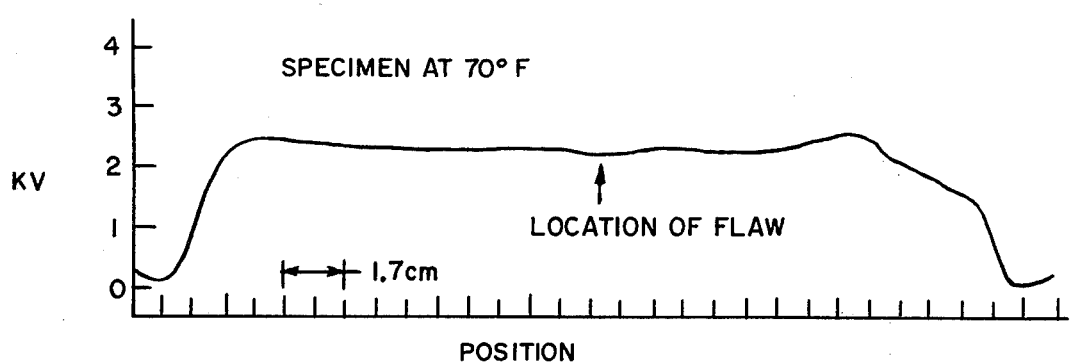
FIG. 5A is a graph illustrating the surface potential across a polyethylene specimen having a 12.5 mm diameter epoxy inclusion for a test conducted at 70° F.

Specimen were prepared similar to that of Example 2 except that the inclusion was about 12.5 mm in diameter. One specimen was run in the apparatus at room temperture (70° F.). After a time lapse of 30 minutes, the surface potential profile was measured as shown in FIG. 5A.

Figure 5B:
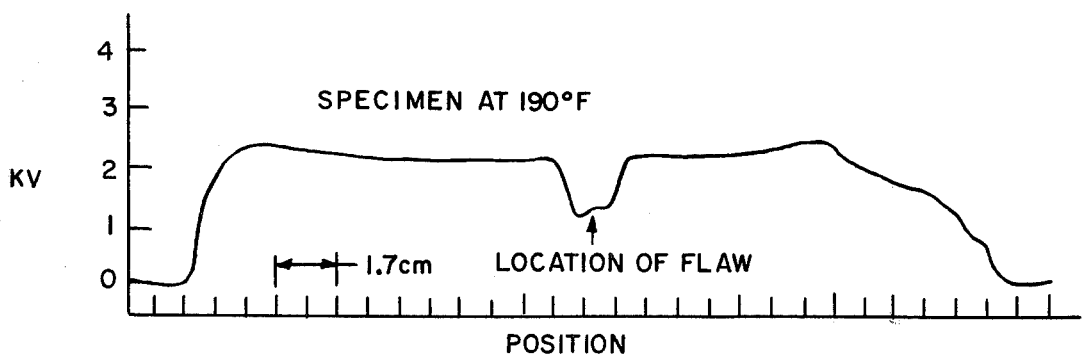
FIG. 5B is a graph illustrating the surface potential across a polyethylene specimen having a 12.5 mm diameter inclusion for a test conducted at 190° F.
Figure 6A:
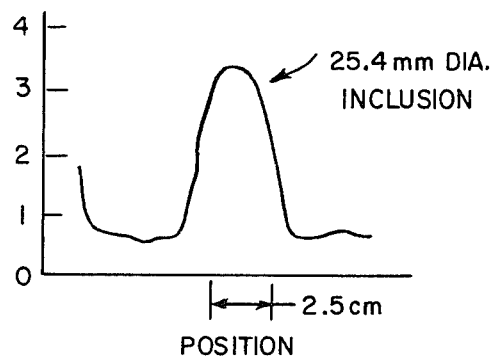
FIGS. 6A, 6B, 6C and 6D are graphs illustrating the surface potential at 75° F. for nylon 6/6 specimen having polyethylene inclusions of varying size.
Figure 6B:
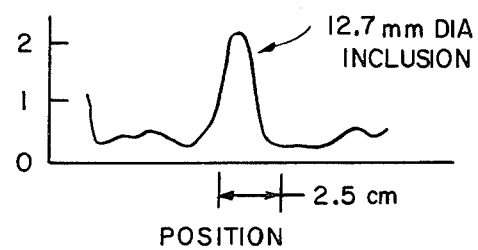
Figure 6C:
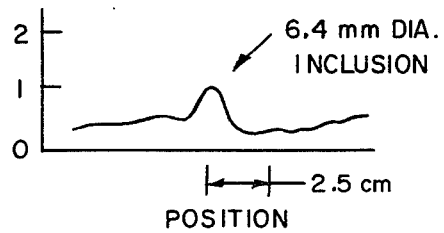
Figure 6D:
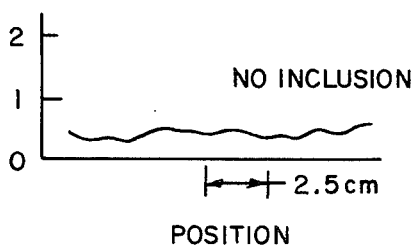

A second specimen was run under the same conditions except that when the surface was charged, the specimen was at 190° F., and maintained at such temperature by heating from the bottom by resistive heater. An image of the inclusion represented by a depression in the surface charge profile showed up immediately after charging and developed with time. After a time lapse of 30 minutes the surface potential profile was then measured as shown in FIG. 5B. Note that the depression of the surface potential in FIG. 5B coincides in location and extent with the 12.5 mm defect.

EXAMPLE 4

Specimen were prepared similar to Example 2 except that Nylon 6/6 was used as the matrix, polyethylene was used for the inclusion and various inclusion sizes from about 6.4 mm to about 25.4 mm were made. The specimen were charged as in Example 1 and the tests were conducted at 25° C.

FIGS. 6A, 6B, 6C and 6D illustrate the surface potential about 60 seconds after charging for specimen having inclusions of 25.4 mm, 12.7 mm, 6.4 mm, and no inclusion, respectively.

EXAMPLE 5

Figure 7A:
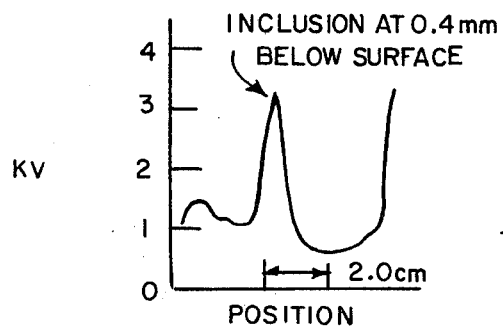
FIGS. 7A, 7B and 7C are graphs illustrating the surface potential at 75° F. for nylon 6/6 specimen having polyethylene inclusions at various distances below the surface.
Figure 7B:
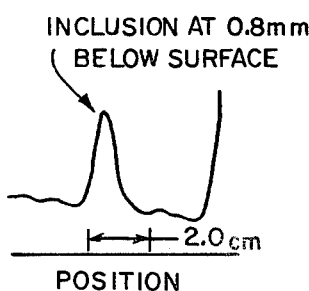
Figure 7C:
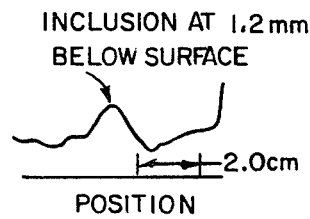

Nylon 6/6 specimen were prepared similar to Example 4 except that the inclusion was 4 mm thick and 6 mm in diameter, and the inclusion was positioned at various depths in the specimen, i.e. 0.4, 0.8 and 1.2 mm, respectively. The specimen were then surface charged as in Example 1 and the specimen were kept at 25° C. After 60 seconds the surface potential was measured. FIGS. 7A, 7B and 7C illustrate the surface potential after 30 minutes for specimen having inclusions at 0.4 mm, 0.8 mm and 1.2 mm, respectively below the surface.

EXAMPLE 6

A nylon 6/6 specimen was prepared similar to Example 4 having an inclusion approximately 6 mm in diamter. The specimen was surface charged as in Example 1 and the surface charge was recorded at various times at 25° C. FIGS. 8A through 8E illustrate the change in surface charge with time.

EXAMPLE 7

The method of this invention can also be applied to determine the quality of adhesive bonds between, for example two insulating materials or between an insulating material and a metallic or conductive substrate.

A specimen was prepared by priming an aluminum panel and coating the primed aluminum with aluminum oxide filled silicon rubber. Certain areas of the panel were not primed in order to create predetermined areas of poor bonding. The specimen was surface charged at 25° C. and the surface charge was recorded 5 seconds later. FIG. 9 illustrates a recording of the surface change. The unprimed areas, i.e. areas of poor bonding, are clearly detected.

EXAMPLE 8

A structural specimen was prepared as illustrated in FIG. 10. A glass reinforced epoxy panel was supported from an aluminum base plate by four (4) ribs of the same glass reinforced epoxy as the panel. Adhesive bonds were made between each rib and the panel and aluminum plate as follows:

| | Quality of Adhesive Bonds | |
| --- | --- | --- |
| | Bond | |
| Rib | Epoxy Panel | Aluminum Plate |
| 1 | Good | Poor |
| 2 | Poor | Poor |
| 3 | Poor | Good |
| 4 | Good | Good |

The surface of the epoxy panel was charged at 25° C. and the surface charge subsequently recorded. FIG. 11 illustrates the recording of the surface charge. Note that the quality of the bonds are differentiated. Thus, the location of poor bonds can be determined.

Thus, it can be seen that non destructive evaluation in accord with the present invention provides very good definition of defect location, size and shape. It can be seen that the method of this invention is useful over a wide range of conductivities (or resistivities) of polymers. Nylon 6/6 is four to five orders of magnitude more conductive than polyethylene. The main criterion for usefulness if the present method is that the material have a long enough time for decay of the surface charge so that subsequent measurements can be made. Thus, for the more conductive materials, such as nylon, the surface charge decay rate is higher and, consequently, the inspection time is much shorter. Furthermore, no heating is required with the more conductive materials because the decay rate is fast enough.

While the present invention has been described in detail along with the preferred embodiments thereof, it will be appreciated that those skilled in the art, upon reading this disclosure, may make modifications and improvements within the spirit and scope of the invention. For instance, although the invention has been illustrated using an apparatus wherein the specimen moves relative to the corona charger and electrostatic probe, it will be appreciated that equivalent results can be obtained by holding the specimen fixed and moving the corona charger and electrostatic probe relative to it.

Further, although the residual charge pattern has been determined by using an electrostatic probe, the residual charge pattern can be visualized by developing it by any of a wide variety of techniques for developing electrostatic images well known in the fields of electrostatic and electrophotographic imaging and copying. The developed image may then be transferred to a receiver sheet. On the other hand the residual charge pattern can first be transferred to a carrier sheet and then developed for visualization. Such techniques and other suitable means for visualizing the residual charge pattern are contemplated by this invention.

In addition, for example, the charge on the surface can be monitored by multiple probes or a single probe with a scanning capability. The data can be processed as long as the initial charge and its decay rate at a given point are known. Irrespective of the uniformity of the initial charge deposition across the whole surface. In some instances it maybe more desirable to determine the charge decay rate of a perfect specimen and analyze other specimen by comparing them with the reference data.

We claim:

1. A method for the nondestructive testing and evaluation of an insulating material, said method comprising the steps of: applying an electrostatic charge pattern to one surface of the material; providing an electrode on a second surface opposite said one surface, said electrode being at an electrical potential lower than said one surface so that the electrostatic charge can decay through said material; allowing the charge pattern to decay for a predetermined period of time; and determining the residual charge pattern on said one surface after said period.

2. The method of claim 1 wherein said material is a polymeric material.

3. The method of claim 2 wherein said material is selected from the group consisting of polyethylene, nylon 6/6 and epoxy.

4. The method of claim 1 wherein the material is held above room temperature during said period.

5. The method of claim 1 wherein said material is heated to a temperature in the range of about 150° F. to about 230° F.

6. The method of claims 1, 2, 3, 4 or 5 wherein the residual charge pattern is determined by scanning the material with an electrostatic probe.

7. The method of claims 1, 2, 3, 4 or 5 wherein the residual charge pattern is determined by developing the charge pattern to form a visible image.

8. A method for the nondestructive testing and evaluation of an insulating material, said method comprising the steps of:
applying an electrostatic charge pattern to one surface of the material;
providing an electrode on a second surface opposite said one surface, said electrode being at an electrical potential lower than said one surface so that the electrostatic charge can decay through said material;
heating the material from said second surface to provide a temperature gradient across said material;
allowing the charge pattern to decay for a predetermined period of time; and determining the residual charge pattern on said one surface after said period.

9. The method of claim 8 wherein said material is a polymeric material.

10. The method of claim 9 wherein said material is selected from the group consisting of polyethylene, nylon 6/6 and epoxy.

11. The method of claim 8 wherein the material is held above room temperature during said period.

12. The method of claim 8 wherein said material is heated to a temperature in the range of about 150° F. to about 230° F.

13. The method of claims 8, 9, 10, 11 or 12 wherein the residual charge pattern is determined by scanning the material with an electrostatic probe.

14. The method of claims 8, 9, 10, 11 or 12 wherein the residual charge pattern is determined by developing the charge pattern to form a visible image.

15. A method for evaluating the bond between an insulating material and another material, said method comprising applying an electrostatic charge to the surface of the insulating material, placing the non-bonded surface of the other material at an electrical potential lower than that of the charged surface of the insulating material, and determining the remaining charge pattern on the surface of the insulating material after a predetermined time period, thereby determining areas of poor bonding between said materials.

* * * * *